(12) United States Patent  
Yamane

(10) Patent No.: US 8,764,641 B2  
(45) Date of Patent: Jul. 1, 2014

(54) PLUG DEVICE AND ENDOSCOPE

(75) Inventor: Kenji Yamane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 36 days.

(21) Appl. No.: 13/432,008

(22) Filed: Mar. 28, 2012

(65) Prior Publication Data

US 2012/0253127 A1    Oct. 4, 2012

(30) Foreign Application Priority Data

Mar. 29, 2011    (JP) ............................... P2011-072203

(51) Int. Cl.
*A61B 1/00*    (2006.01)
*A61M 5/178*    (2006.01)

(52) U.S. Cl.
CPC ......... *A61B 1/00131* (2013.01); *A61B 1/00137* (2013.01)
USPC ..................................... 600/154; 604/167.05

(58) Field of Classification Search
CPC . A61B 1/00137; A61M 39/20; A61M 39/221
USPC .......................... 600/154; 604/167.01–167.06
See application file for complete search history.

(56) References Cited

U.S. PATENT DOCUMENTS 4,632,110 A * 12/1986 Sanagi .......................... 606/207
4,715,360 A * 12/1987 Akui et al. .................... 600/154
5,632,735 A * 5/1997 Wyatt et al. ................... 604/539

FOREIGN PATENT DOCUMENTS

JP    2005-224529 A    8/2005
JP    2008-043774 A    2/2008

* cited by examiner

*Primary Examiner* — Alireza Nia
*Assistant Examiner* — Timothy J Neal
(74) *Attorney, Agent, or Firm* — Birch, Stewart, Kolasch & Birch, LLP

(57) ABSTRACT

A portion of an outer periphery of a plug body of a forceps plug is cut out to form an arm having a shape along the circumferential direction of an outer peripheral surface of an opening. A tip portion of the arm is formed with a boss that protrudes toward the opening. An outer peripheral surface of the opening tip portion is formed with a cam groove for a forceps plug that guides the boss. The cam groove for a forceps plug is constituted by a cam groove for attachment that guides the boss 33 when the forceps plug is attached, a cam groove for locking that locks the boss, and a cam groove for removal that guides the boss when the forceps plug is removed. When the boss moves along the cam groove for removal, the deflection of the arm exceeds an elastic limit, and the arm breaks.

21 Claims, 22 Drawing Sheets

PLUG DEVICE AND ENDOSCOPE

BACKGROUND OF THE INVENTION

1. Field of the Invention

The present invention relates to a plug device in which a plug body unit is detachably attached to the opening portion of a channel within an endoscope, and an endoscope equipped with this plug device.

2. Description of the Related Art

Until now, in the medical field, an insertion part of an endoscope is inserted into the inside of the body of a patient to perform not only the observation of the inside of the body but also various kinds of treatment on the parts being observed. Specifically, various kinds of treatment, such as incision or collection of observed parts, is performed by inserting treatment tools, such as forceps and an incision implement, through a forceps channel within the insertion part from a forceps port opening provided at a manipulating part of the endoscope, and projecting the treatment tools from the tip of the insertion part.

A forceps plug through which a treatment tool can be inserted, when a treatment is performed, is attached to the forceps port opening. This forceps plug prevents body fluid, filth, air, or the like flowing back within the forceps channel and leaking out to the outside from the forceps port opening, due to changes in internal pressure within the body. As such a forceps plug, a disposable forceps plug which is unreusable so as to be replaced with a new one for each use from a viewpoint of preventing the infection caused by the adhesion of body fluid or the like is generally known.

JP2008-043774A and JP2005-224529A disclose a forceps plug that becomes removable from the forceps port opening by breaking a portion of the plug body unit. In the forceps plugs of JP2008-043774A and JP2005-224529A, reuse becomes impossible because the removal from the forceps port opening is accompanied by destruction. As a result, a used forceps plug is prevented from being erroneously reused.

SUMMARY OF THE INVENTION

In the forceps plugs of JP2008-043774A and JP2005-224529A, since it is necessary to separately perform the manipulation to destroy a portion of a forceps plug and the manipulation to remove the forceps plug, respectively, when the forceps plug is removed from the forceps port opening, there is a problem in that the removal of the forceps plug requires substantial time and effort.

The present invention has been made in view of the above-mentioned problems and an object of the present invention is to provide a plug device that can easily perform the removal and destruction of a forceps plug or the like of a plug body unit for an endoscope, and an endoscope equipped with this plug device.

In order to achieve the above object, the plug device of the present invention is a plug device provided at an outer surface of an endoscope and having a tubular opening portion that leads to a channel within the endoscope and a plug body unit detachably attached to the opening portion. The plug device includes a tubular plug body provided at the plug body unit and having a fitting hole to which the opening portion fits; an arm formed by cutting out a portion of the plug body and extending along an outer peripheral surface of the opening portion fitting into the fitting hole; a boss provided at a tip portion of the arm and protruding toward an outer peripheral surface of the opening portion; a locking groove formed at the outer peripheral surface of the opening portion and locking the boss when the opening portion fits to the fitting hole; and a cam groove formed at the outer peripheral surface of the opening portion continuously with the locking groove and guiding the boss in a direction in which the deflection of the arm increases from the locking groove with the displacement of the plug body unit by removal manipulation of the plug body unit. Until the boss reaches an end point of the cam groove, the boss is guided, the deflection of the arm exceeds an elastic limit, and the arm is broken. In addition, the tubular shape means a hollow tubular shape, and the cross-section orthogonal to the axis direction thereof is, for example, circular, elliptical, polygonal, or the like.

Preferably, the outer peripheral surface of the opening portion is provided with a guide groove that extends to the locking groove in an oblique direction that inclines with respect to the axial direction of the opening portion from a opening portion tip position in the tip of the opening portion that is offset in the first circumferential direction with respect to the locking groove, and that guides the boss to the locking groove, and the boss engages the guide groove from the opening portion tip position, and moves to the locking groove along the guide groove when the plug body unit is rotated after the engagement in a second circumferential direction opposite to the first circumferential direction. In addition, the "shape extending in the oblique direction" means a shape that extends in a direction that inclines with respect to the axial direction of the opening portion, and specifically includes not only a shape that extends in the shape of a straight line in the direction that inclines with respect to the axial direction of the opening portion, but also a shape that extends in the direction that inclines with respect to the axial direction of the opening portion as a whole, though extending in a zig zag manner or like a wave manner.

Preferably, the fitting is completed when the opening portion proceeds to the back of the fitting hole and the boss moves to the locking groove, with the movement of the boss along the guide groove.

Preferably, the guide groove has a shape that maintains the deflection of the arm accompanying the movement of the boss within the elastic limit.

Preferably, the locking groove extends toward the tip of the opening portion from the end point of the guide groove.

Preferably, the cam groove extends from the locking groove in the oblique direction that inclines with respect to the axial direction of the opening portion to a groove end point position that is offset closer to the second circumferential direction at the rear end side of the opening portion than the locking groove, and as the plug body unit is rotated in the second circumferential direction after the locking of the boss by the locking groove, the boss is guided to the cam groove from the locking groove, and moves toward the groove end point position along the cam groove.

Preferably, the outer peripheral surface of the opening portion is provided with a guide groove that extends in the axial direction of the opening portion toward the rear end side of the opening portion from a opening portion tip position in the tip of the opening portion that is offset in the first circumferential direction with respect to the locking groove, the inner surface of the plug body is provided with a guide protrusion that engages the guide groove from the opening portion tip position, the boss and the locking groove are located on the same straight line parallel to the axial direction of the opening portion when the guide protrusion engages the guide groove, and the boss rises over the outer peripheral surface of the opening portion from the tip of the opening portion and moves to the locking groove as the plug body unit is moved in a first direction that faces the rear end side of the opening portion in a state where the guide protrusion engages the guide groove.

Preferably, the cam groove extends from the locking groove in the oblique direction that inclines with respect to the axial direction of the opening portion to a groove end point position that is offset closer to a second circumferential direction opposite to the first circumferential direction at the tip of the opening portion than the locking groove, and as the plug body unit is moved in the second circumferential direction opposite to the first circumferential direction after the locking of the boss by the locking groove, the boss is guided to the cam groove from the locking groove, and moves toward the groove end point position along the cam groove.

Preferably, the channel is a treatment tool channel through which a treatment tool is inserted.

Additionally, an endoscope of the present invention includes an insertion part to be inserted into a body to be examined, a channel to be inserted through the interior of the insertion part, and the plug device according to any one of the above aspects.

In the plug device and endoscope of the present invention, the boss is guided by the cam groove connected to the locking groove that locks the boss in a direction in which the deflection of the arm increases with the removal manipulation of the plug body unit, and the deflection of the arm exceeds an elastic limit and the arm breaks until the boss reaches the end point. Thus, a portion of the plug body unit can be automatically destructed in the middle of the removal manipulation of the plug body unit. As a result, removal and destruction of the plug body unit can be easily executed than in the related art.

DESCRIPTION OF THE PREFERRED EMBODIMENTS

Figure 1:
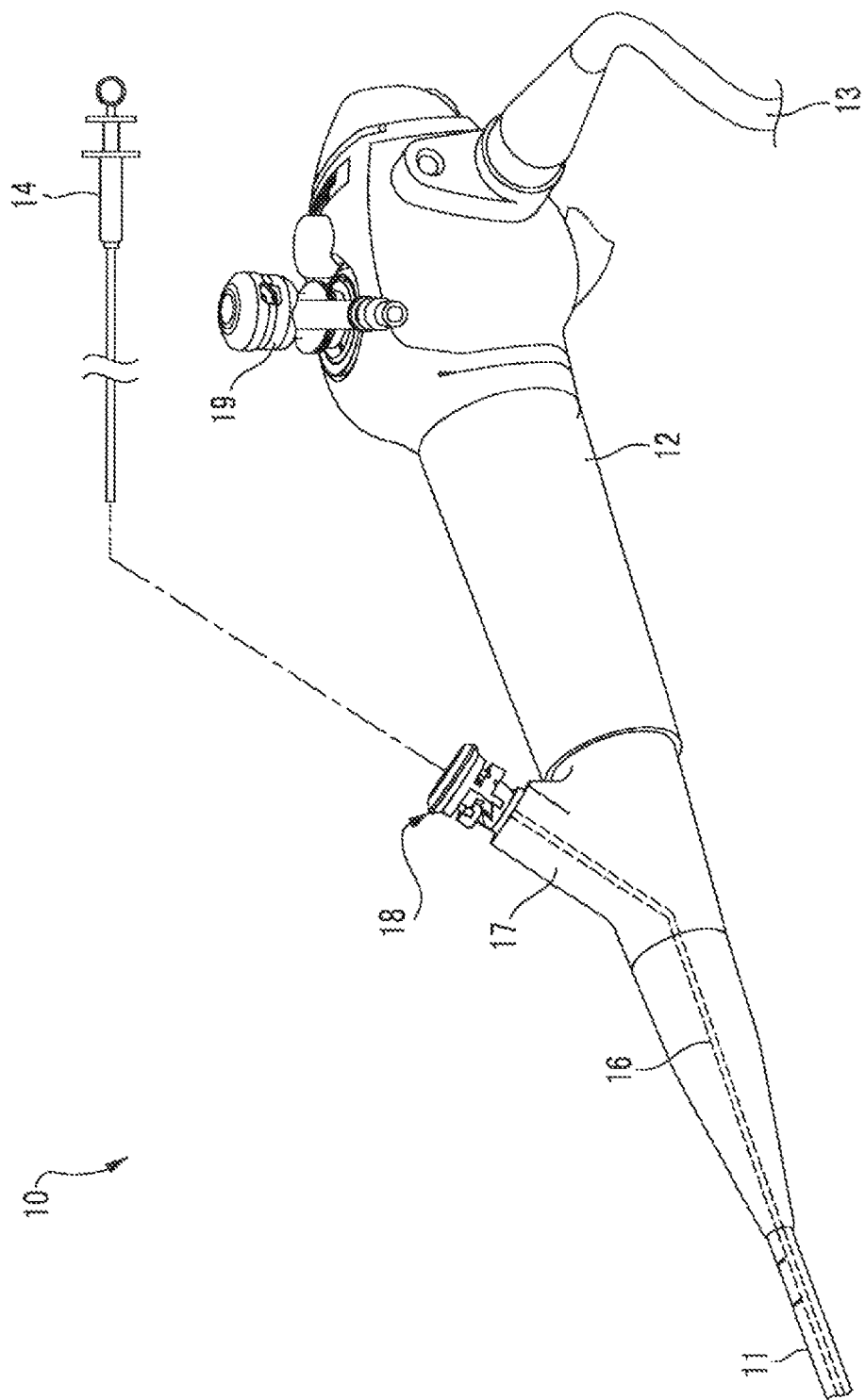
FIG. 1 is a perspective view of an endoscope.
Figure 2:
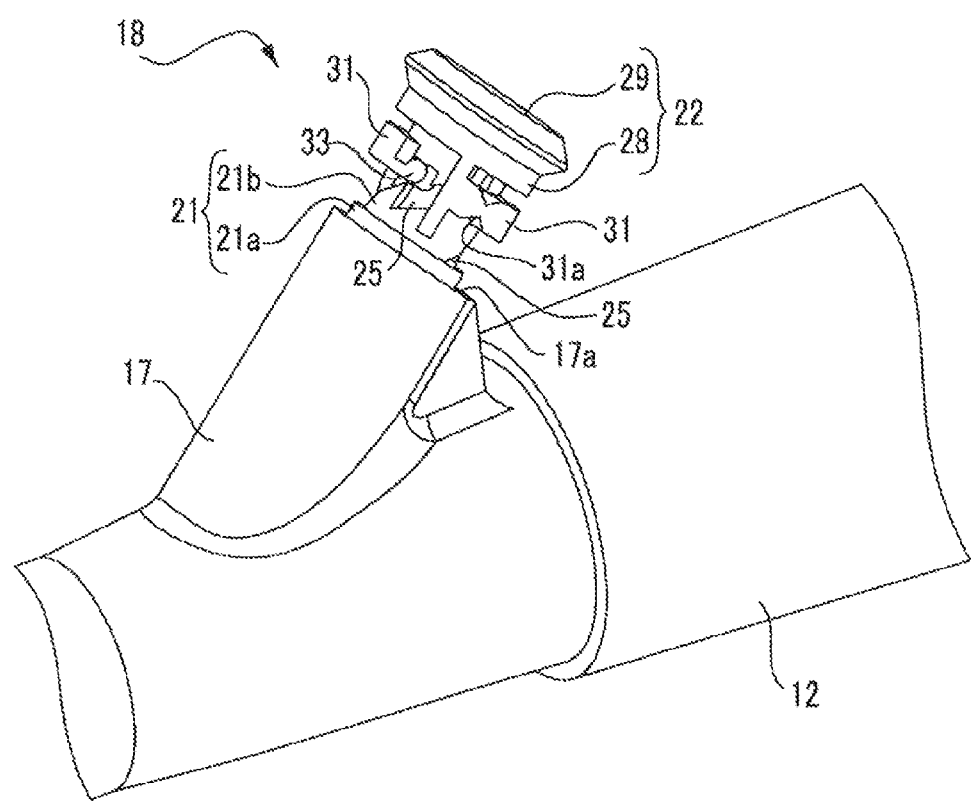
FIG. 2 is a perspective view of a forceps plug device.
Figure 3:
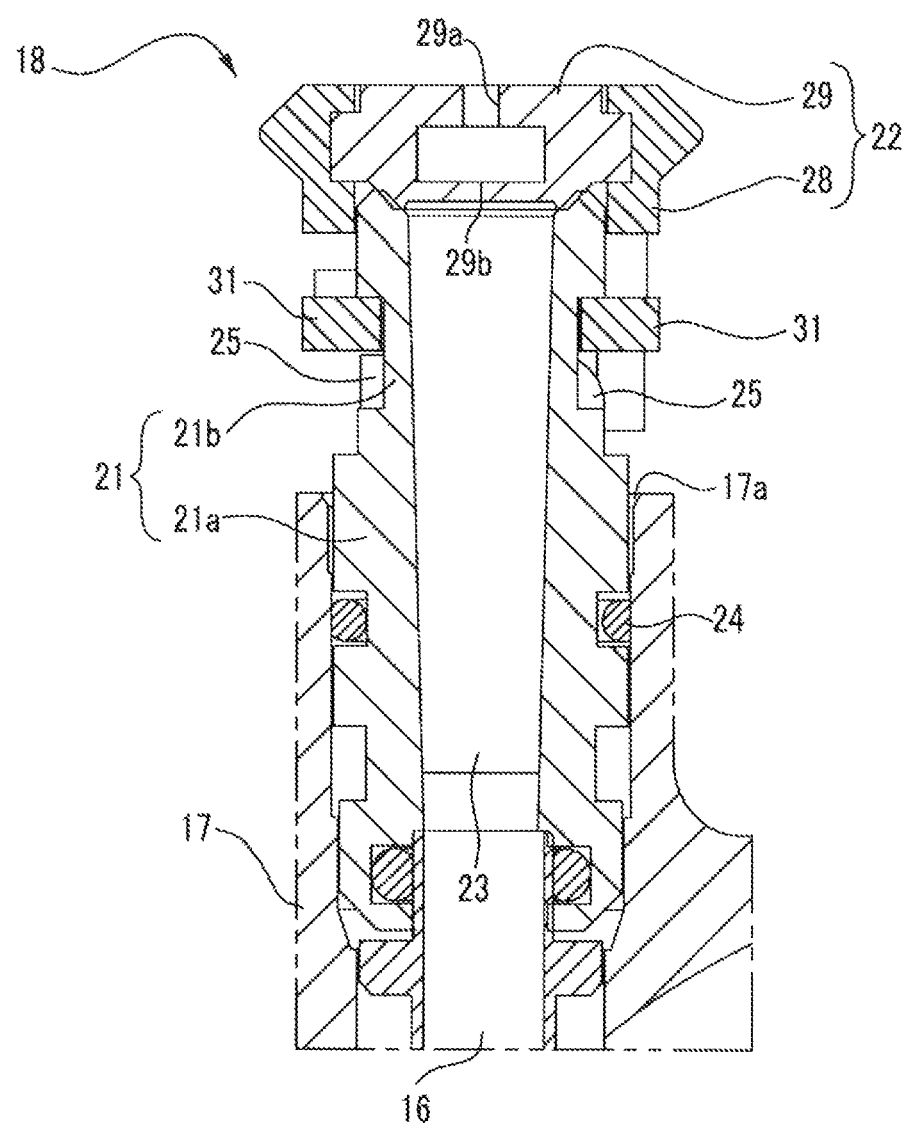
FIG. 3 is a cross-sectional view of the forceps plug device.
Figure 4:
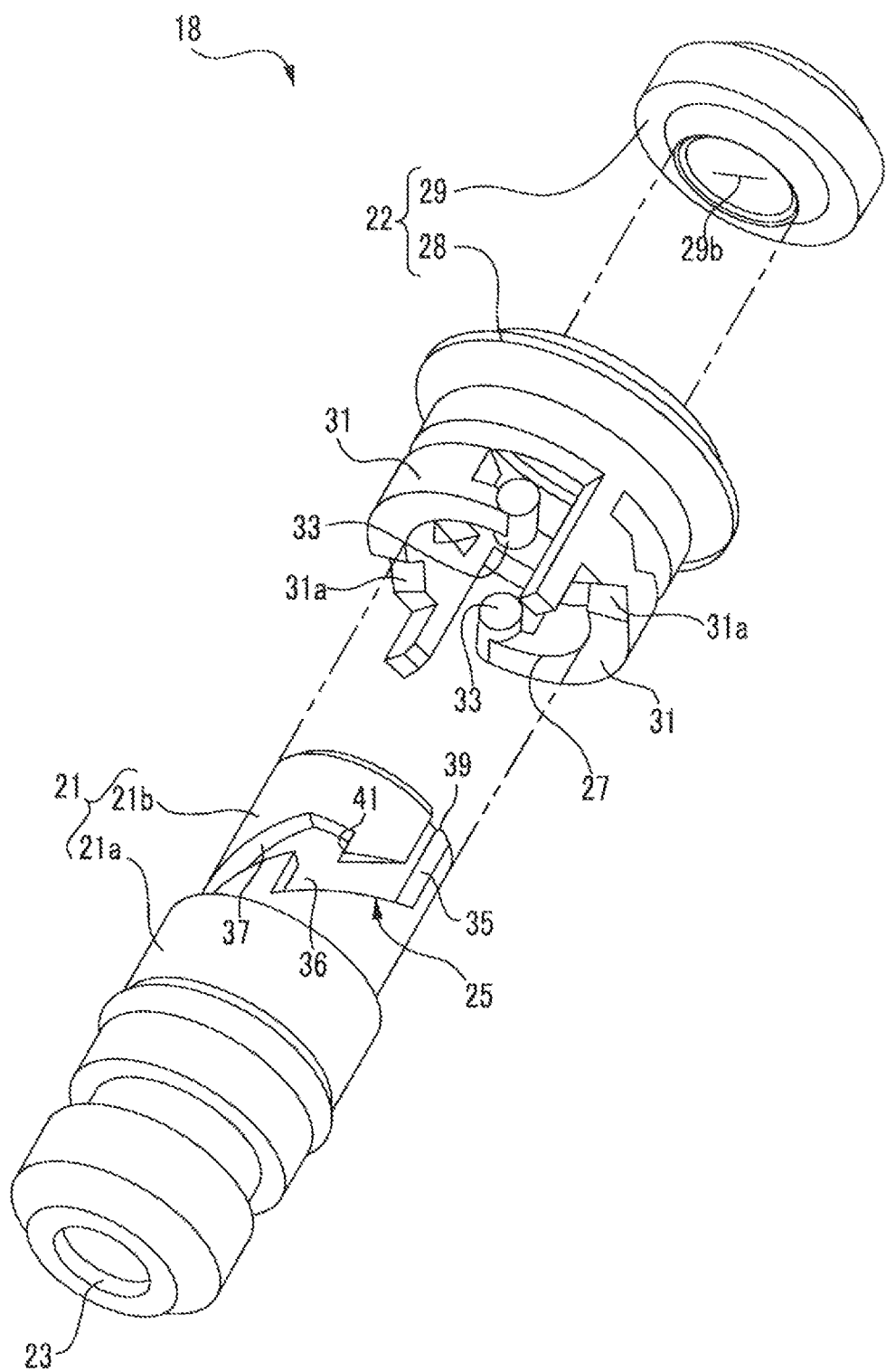
FIG. 4 is an exploded perspective view of the forceps plug device seen from the opening side.
Figure 5:
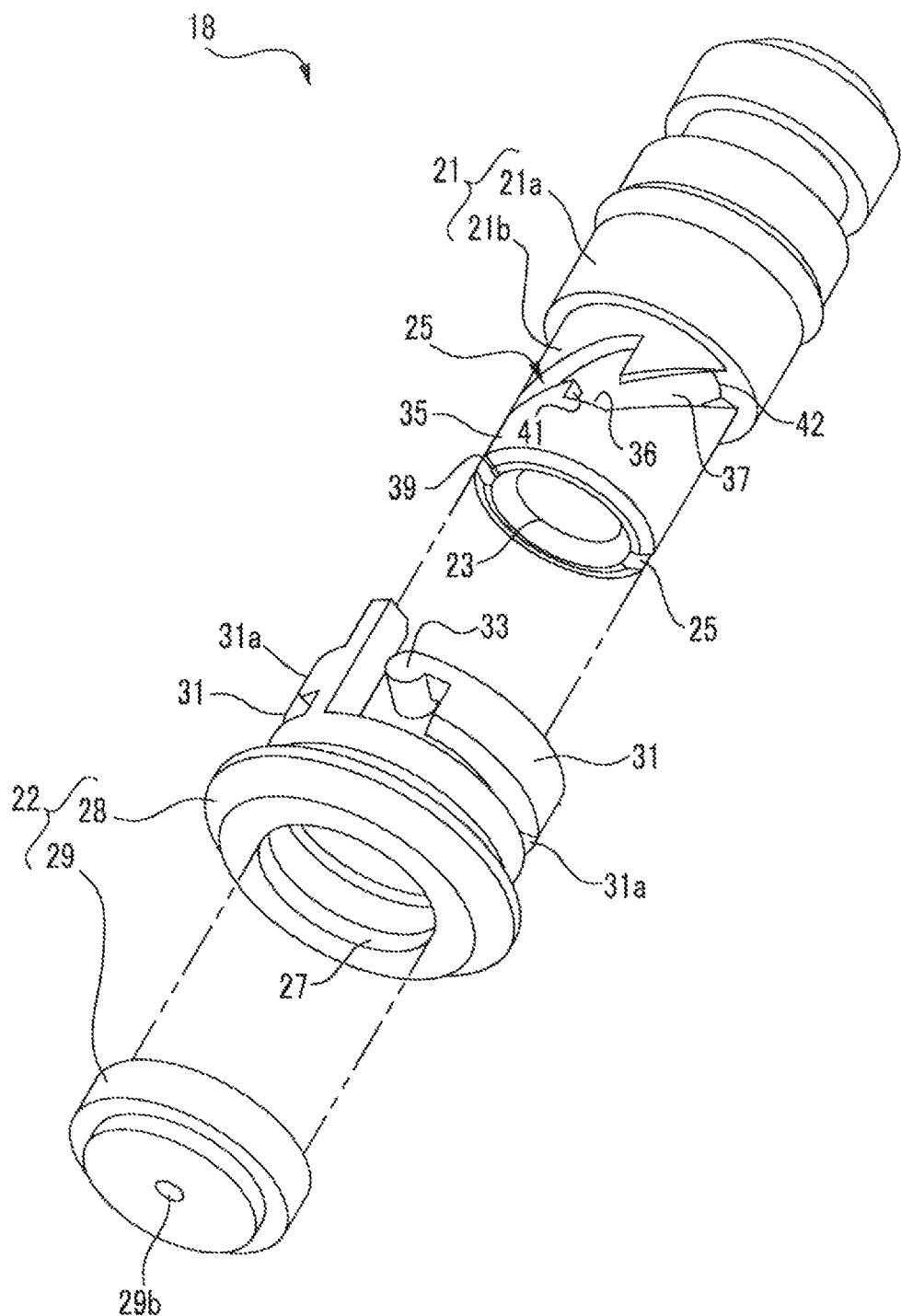
FIG. 5 is an exploded perspective view of the forceps plug device seen from the forceps plug side.

As shown in FIG. 1, an endoscope 10 is, for example, a bronchoscope to be inserted into the tracheal, and includes an insertion part 11 to be inserted into the tracheal, a manipulating part 12 continuously provided at a base end portion of the insertion part 11, and a universal cord 13 connected to the manipulating part 12. The universal cord 13 is connected to a processor device, a light source device, or the like that is not shown.

A forceps channel 16 for allowing a treatment tool 14, such as forceps, to be inserted therethrough is disposed within the insertion part 11. One end of the forceps channel 16 opens at the tip face of the insertion part 11, and the other end thereof is connected to a forceps port 17 provided at the manipulating part 12. An inlet of the forceps port 17 is provided with a forceps plug device 18.

Additionally, the forceps channel 16 is also used as a path for suctioning body fluids, such as blood, solids, such as filth in the body, or the like from the opening of the tip face of the insertion part 11. A suction channel (not shown) that branches from the forceps channel 16 is disposed within the manipulating part 12, and this suction channel is connected to a suction button 19 provided at the manipulating part 12.

The suction button 19 is connected a negative pressure source (not shown) out of the manipulating part 12. The suction button 19 switches the communication/blocking between the suction channel and the negative pressure source by pressure manipulation or release of the pressure manipulation.

As shown in FIGS. 2 to 5, the forceps plug device 18 is equivalent to the opening portion of the present invention, and includes a forceps port opening (hereinafter simply referred to as a opening) 21 fixed to an inlet of the forceps port 17, and a disposable forceps plug (plug body unit) 22 detachably mounted on the opening 21.

The opening 21 has an inner conduit 23 that leads to the forceps channel 16, and includes a opening body portion 21a fixed to the interior of an aperture 17a of the forceps port 17, and a opening tip portion 21b that protrudes to the near side of the aperture 17a. Packing 24 that prevents leakage of a body fluid or like from a gap with an inner peripheral surface of the forceps port 17 is fitted to an outer peripheral surface of the opening body portion 21a. Hereinafter, the near side of the aperture 17a is referred to as a "tip direction", and the depth direction of the aperture 17a is referred to as a "rear end direction". Additionally, the end and end face of each portion of the opening 21 and the forceps plug 22 on the side of the tip direction are referred to as a tip portion and a tip face, respectively, and the end and end face of each portion on the side of the rear end direction are referred to a rear end portion and a rear end face, respectively.

The opening tip portion 21b is formed so as to have an external diameter that is somewhat smaller than the external diameter of the opening body portion 21a. A pair of cam grooves 25 for a forceps plug is formed at pitch intervals of 180° in the outer peripheral surface of the opening tip portion 21b. The cam grooves 25 for a forceps plug is used for attachment, fixation, and removal of the forceps plug 22. Hereinafter, the clockwise direction as seen from the forceps port 17 side among the circumferential directions of the outer peripheral surface of the opening tip portion 21b is referred to as a first circumferential direction, and the counterclockwise direction is referred to as a second circumferential direction.

The forceps plug 22 is formed from, for example, various kinds of elastic materials, such as resin. The forceps plug 22 includes a tubular plug body 28 having a fitting hole 27 to which the opening tip portion 21b, and a cap 29 that fits to the opening on the side of the tip direction of the fitting hole 27.

A pair of arms 31 is formed at pitch intervals of 180° at the plug body 28 by cutting out a portion of the outer periphery of the plug body. The arm 31 extends long along the first circumferential direction of the outer peripheral surface of the opening tip portion 21b. A root portion of the arm 31 is formed with a low-strength portion 31a of which the width of the arm 31 is smaller than that of the other portions. Thereby, the arm 31 becomes easy to break at the low-strength portion 31a. The width of the arm 31 is adjusted so that the low-strength portion 31a breaks when the deflection of the arm 31 exceeds a certain size.

Additionally, the tip portion of the arm 31 is formed with a boss 33 that protrudes along the outer peripheral surface of the opening tip portion 21b. The boss 33 engages the cam groove 25 for a forceps plug.

The cap 29 has a cylinder shape of which both ends are blocked. The tip face of the cap 29 is formed with a small hole 29a, and the rear end face thereof is formed with a slit 29b. The small hole 29a is formed so as to have a smaller diameter than the external diameter of the treatment tool 14.

The slit 29b is brought into a close contact state by the elastic force of the cap 29 to hold a watertight or airtight state when the treatment tool 14 is not inserted therethrough. On the other hand, the slit 29b is brought into a state where the inner peripheral surface of the slit is brought into close contact with the outer peripheral surface of the treatment tool 14 by the elastic force of the cap 29, to prevent the leakage caused by the backflow of a body fluid or the like, in a state where the treatment tool 14 is inserted therethrough. The small hole 29a and the slit 29b are coaxially arranged on the inner conduit 23 when the opening tip portion 21b fits to the fitting hole 27. For this reason, the treatment tool 14 is inserted into the forceps channel 16 through the small hole 29a, the slit 29b, and the inner conduit 23.

The rear end face of the cap 29 becomes a face on which the tip of the opening tip portion 21b abuts when the opening tip portion 21b fits to the fitting hole 27.

Figure 6:
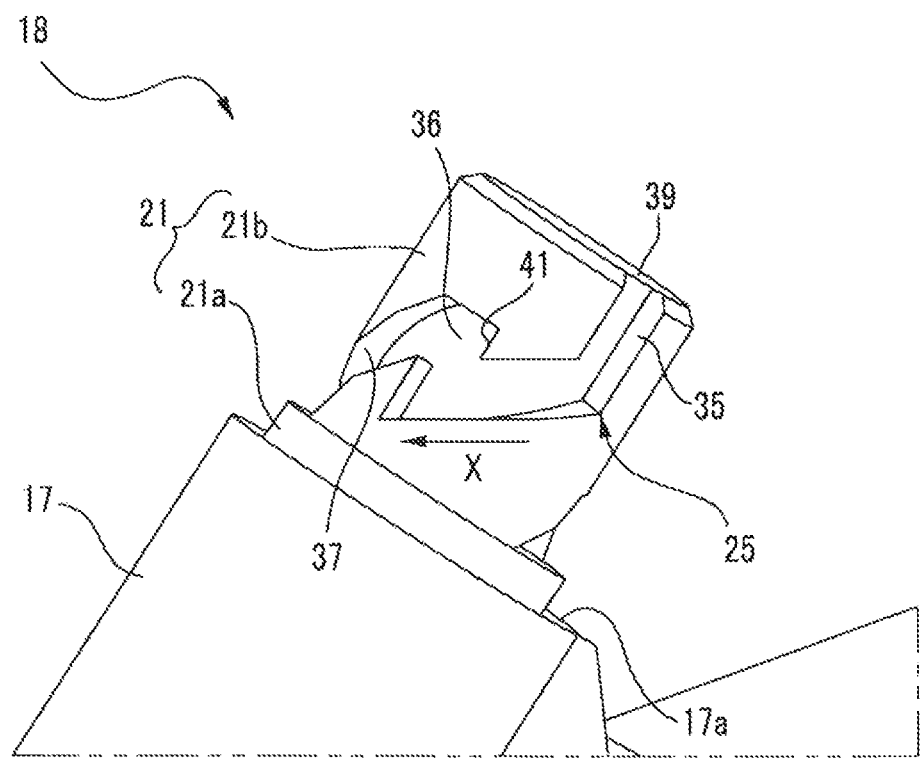
FIG. 6 is a perspective view of a cam groove for a forceps plug.

As shown in FIG. 6, the cam groove 25 for a forceps plug guides the boss 33 at the time of attachment, fixation, and removal of the forceps plug 22. The cam groove 25 for a forceps plug roughly includes a cam groove for attachment (guide groove) 35, a cam groove for locking (locking groove) 36, and a cam groove for removal 37 equivalent to the cam groove of the present invention.

The cam groove 35 for attachment is formed at a position that is offset toward the first circumferential direction with respect to the cam groove 36 for locking, and guides the boss 33 to the cam groove 36 for locking. The cam groove 35 for attachment has a V-shape that extends in the rear end direction along the axial direction (hereinafter simply referred to as a opening axial direction) of the opening 21 from the opening tip position (opening portion tip position) 39 at the tip of the opening tip portion 21b and that further extends in an oblique direction X that inclines with respect to the axial direction of the opening portion between the rear end direction and the second circumferential direction from there. A groove end point of the cam groove 35 for attachment is located slightly closer to the downward side than the central portion of the opening tip portion 21b.

Additionally, the cam groove 35 for attachment deflects the arm 31 via the boss 33 when the boss 33 guided in the oblique direction X that inclines with respect to the axial direction of the opening portion. In this case, the inclination angle or the position of the groove end point in the cam groove 35 for attachment is adjusted so that the deflection of the low-strength portion 31a does not exceed an elastic limit. Here, the elastic limit means the magnitude of a limit force such that the deflected low-strength portion 31a does not restore to its original shape.

The cam groove 36 for locking locks the boss 33. The cam groove 36 for locking has a shape that extends in the tip direction from the groove end point of the cam groove 35 for attachment. The length of the cam groove 36 for locking is formed so as to be longer than the diameter of the boss 33. Additionally, a regulating portion 41 that regulates movement of the boss 33 in first circumferential direction is formed between the cam groove 35 for attachment and the cam groove 36 for locking.

The cam groove 37 for removal is formed at a position that is offset in the second circumferential direction with respect to the cam groove 36 for locking. The cam groove 37 for removal has a shape that extends in the oblique direction X that inclines with respect to the axial direction of the opening portion from the groove end point of the cam groove 36 for locking, and reaches the groove end point position 42 that is offset closer to the second circumferential direction than the cam groove 36 for locking at the rear end of the opening tip portion 21b (refer to FIG. 5). The cam groove 37 for removal deflects the arm 31 via the boss 33 when the boss 33 is guided similarly to the cam groove 35 for attachment. The inclination angle or groove end point position 42 in the cam groove 37 for removal is adjusted so that the low-strength portion 31a breaks when the deflection thereof exceeds an elastic limit until the boss 33 reaches the groove end point position 42.

Next, the operation of the forceps plug 22 having the above configuration, particularly the attachment and removal processing of the forceps plug device 18 to/from the opening 21 will be described.

Figure 7:
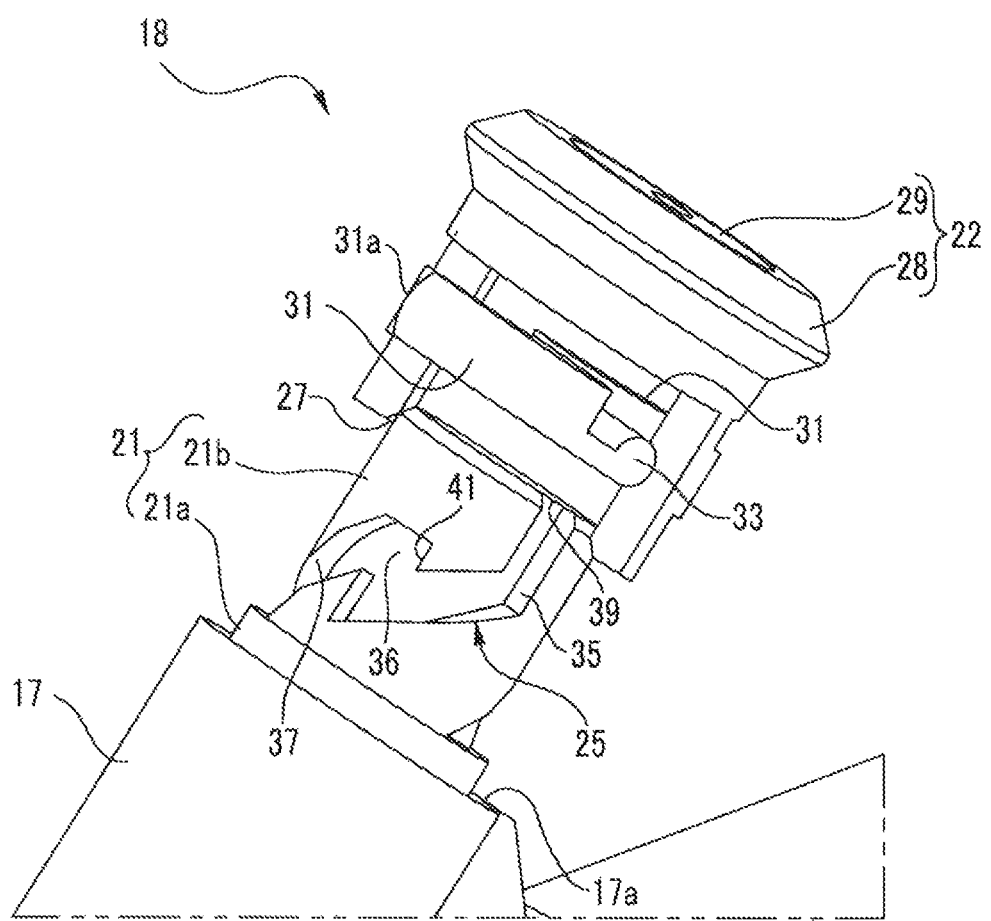
FIG. 7 is an explanatory view for explaining the positioning between a forceps plug and an opening.
Figure 8:
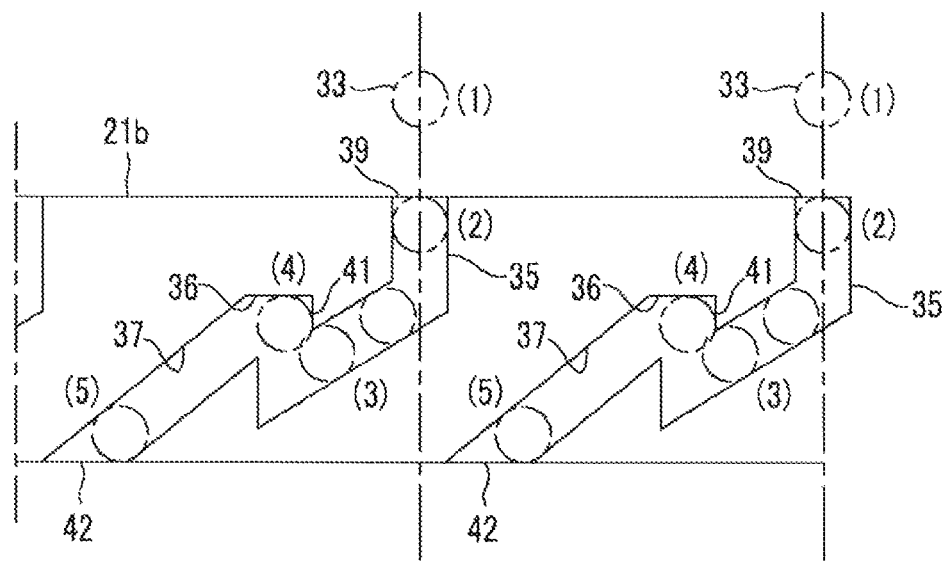
FIG. 8 is an explanatory view for explaining the movement of a boss within the cam groove for a forceps plug.

As shown by the number (1) in parentheses of FIGS. 7 and 8, the positioning of the forceps plug 22 is first adjusted so that the center of the fitting hole 27 coincides with the center of the opening tip portion 21b, and then, the positioning of the forceps plug 22 is performed so that the boss 33 is located substantially above the opening tip position 39.

Figure 9:
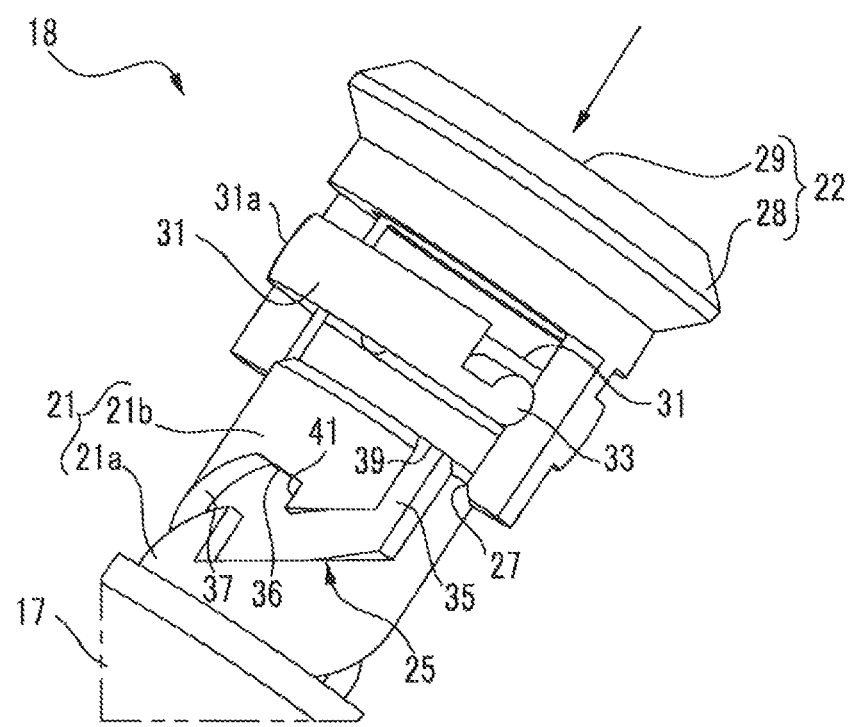
FIG. 9 is an explanatory view for explaining the manipulation of pushing the forceps plug.

After the positioning of the forceps plug 22, as shown by the number (2) in parentheses of FIG. 8, and as shown in FIG. 9, the forceps plug 22 is pressed against the opening tip portion 21b. Thereby, the tip of the opening tip portion 21b is inserted into the fitting hole 27, and the boss 33 is guided into the cam groove 35 for attachment from the opening tip position 39. If the pressing manipulation is continued, the boss 33 moves to a bent portion along the cam groove 35 for attachment, and the tip of the opening tip portion 21b is further inserted into the back of the fitting hole 27.

Figure 10:
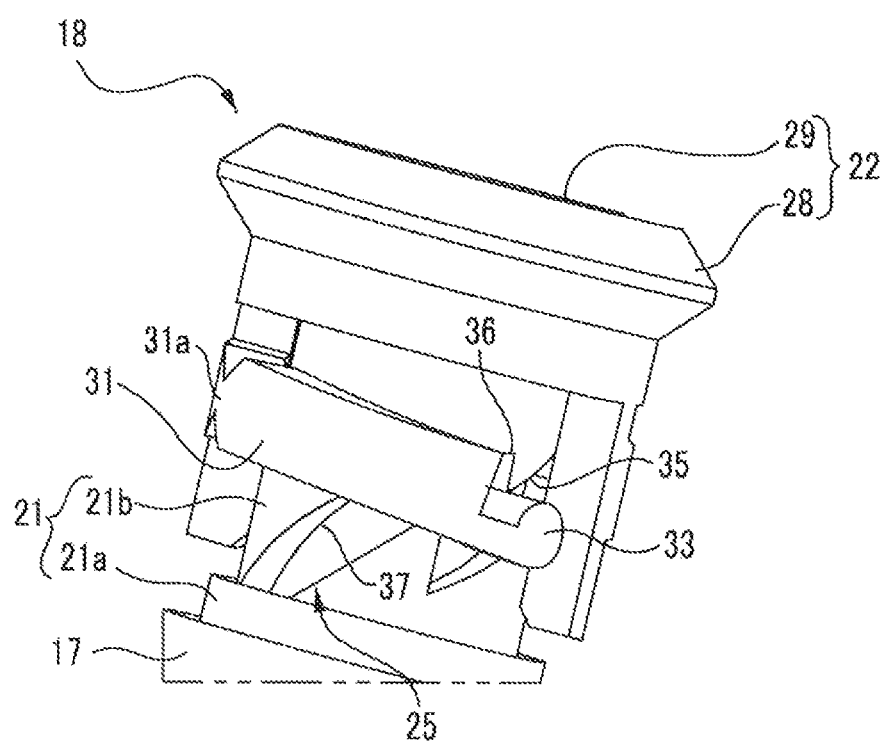
FIG. 10 is an explanatory view for explaining the movement path of the boss that moves along a cam groove for attachment.

After the boss 33 moves to the bent portion of the cam groove 35 for attachment, the rotation manipulation of rotating the forceps plug 22 in the second circumferential direction is made. Thereby, as shown by the number (3) in parentheses of FIG. 8, and as shown in FIG. 10, the boss 33 moves in a direction that turns to the cam groove 36 for locking. With this movement, the arm 31 deflects in the shape of an arc on the side of the opening body portion 21a, and the tip of the opening tip portion 21b is further inserted into the back of the fitting hole 27. The amount of deflection of the arm 31 increases gradually as the travel distance of the boss 33 increases. Since the deflection of the low-strength portion 31a does not exceed an elastic limit until the boss 33 reaches the cam groove 36 for locking, the low-strength portion 31a does not break.

Figure 11:
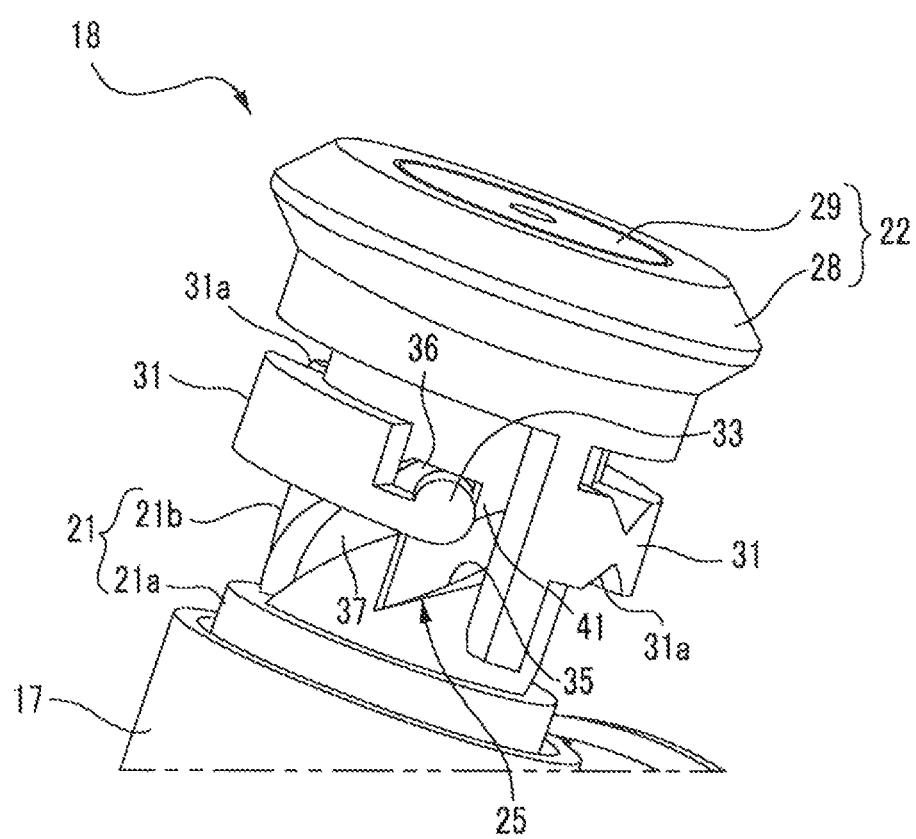
FIG. 11 is an explanatory view for explaining a state where the boss is locked to a cam groove for locking.

Since the inlet of the cam groove 36 for locking opens if the boss 33 reaches the groove end point of the cam groove 35 for attachment in a state where the arm 31 has deflected, the arm is restored to its original shape. Thereby, as shown by the number (4) in parentheses of FIG. 8, and as shown in FIG. 11, the boss 33 is guided into the cam groove 36 for locking. Additionally, when the boss 33 reaches the groove end point of the cam groove 35 for attachment, the fitting of the opening tip portion 21b to the fitting hole 27 is completed.

As the cam groove 36 for locking locks the boss 33, the forceps plug 22 is fixed to the opening 21. Additionally, since the regulating portion 41 abuts on the boss 33 at this time, the forceps plug 22 cannot be rotated in the first circumferential direction, and when the forceps plug is forcedly rotated, the low-strength portion 31a breaks. For this reason, since the boss 33 is prevented from tracing back the cam groove 35 for attachment, the forceps plug 22 is prevented from separating from the opening 21 due to an erroneous operation.

The attachment processing of the forceps plug 22 is completed above. Then, after the treatment tool 14 is inserted into the forceps channel 16 from the forceps plug 22 and various kinds of treatment are performed, removal processing of the forceps plug 22 is started.

First, the rotation manipulation of rotating the forceps plug 22 in the second circumferential direction is made. Thereby, the locking of the boss 33 by the cam groove 36 for locking is released, and the boss 33 is guided into the cam groove 37 for removal. Succeedingly, if the forceps plug 22 is rotated in the second circumferential direction, the boss 33 moves toward the groove end point position 42 along the cam groove 37 for removal.

Figure 12:
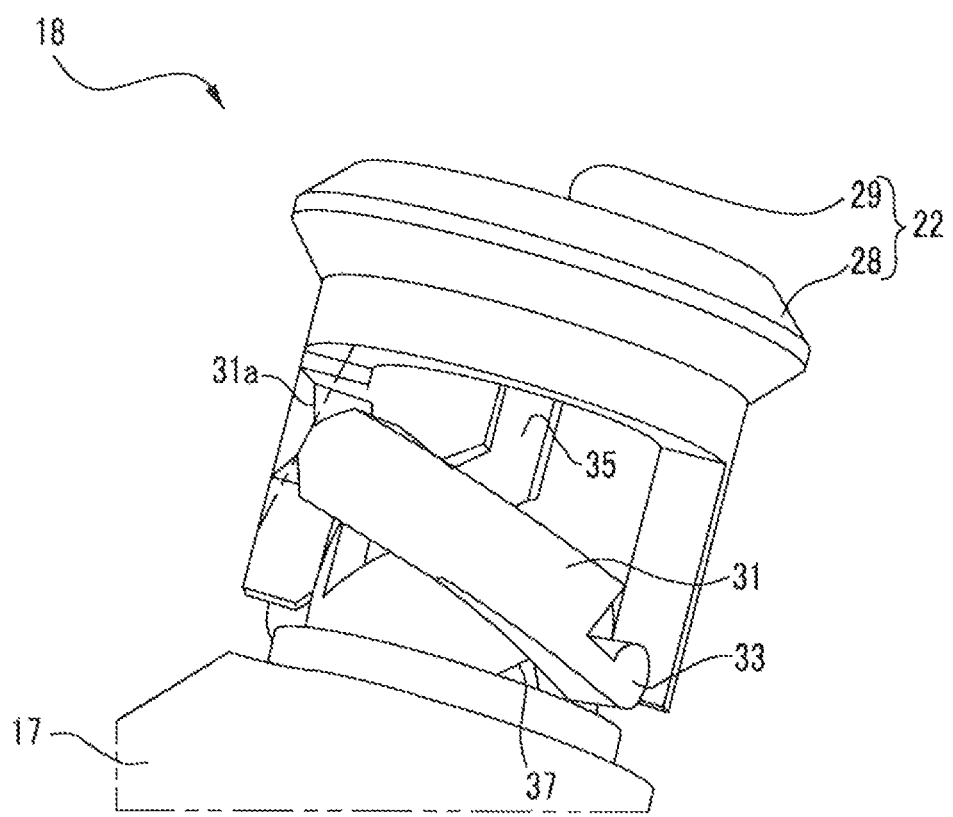
FIG. 12 is an explanatory view for explaining a state when the boss is guided along a cam groove for removal.

As shown in the number (5) in parentheses of FIG. 8 and as shown in FIG. 12, the arm 31 moves in the shape of a circular arc toward the opening body portion 21a with the movement of the boss 33, and this amount of deflection increases as the travel distance of the boss 33 increases. Then, the deflection of the low-strength portion 31a exceeds an elastic limit, and the low-strength portion 31a breaks until the boss 33 reaches the groove end point position 42. Thereby, the forceps plug 22 is in a free state with respect to the opening 21. Next, the manipulation of pulling the forceps plug 22 toward the tip direction is made, and the forceps plug 22 is removed from the opening 21.

Since the arm 31 of the forceps plug 22 removed from the opening 21 is brought into a broken state, the boss 33 is eliminated, and the forceps plug cannot be fixed to the opening 21 again. As a result, the used forceps plug 22 is prevented from being erroneously reused. Since a portion of the forceps plug 22 can be automatically in the middle of the removal manipulation of the forceps plug, removal and destruction of the forceps plug 22 can be executed more simply than those in the rerated art.

[Second Embodiment]

Figure 13:
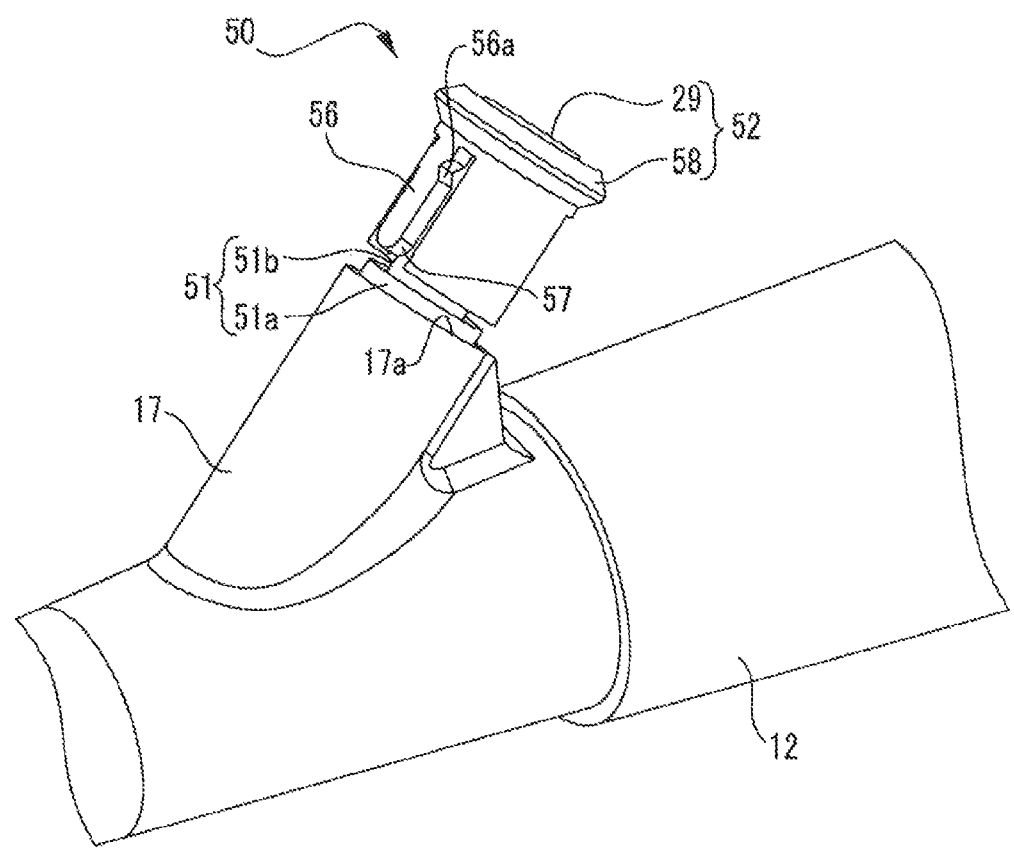
FIG. 13 is a perspective view of a forceps plug device of a second embodiment.
Figure 14:
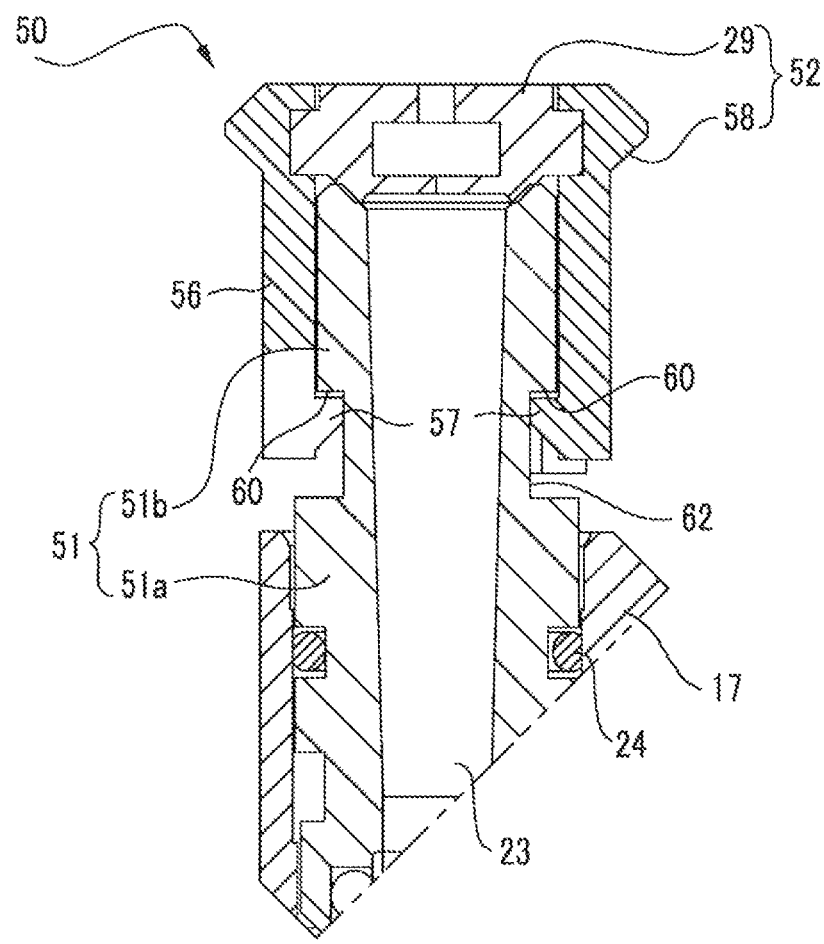
FIG. 14 is a cross-sectional view of the forceps plug device of the second embodiment.

Next, a forceps plug device 50 of a second embodiment of the present invention will be described with reference to FIGS. 13 and 14. In the above first embodiment, the attachment, fixation, removal, and destruction of the forceps plug 22 to the opening 21 are performed in order by rotating the forceps plug 22. However, in the forceps plug device 50, the series of processing are executed by moving the forceps plug along a opening axial direction. In addition, since the forceps plug device 50 fundamentally has the same configuration as the forceps plug device 18 of the first embodiment, the same components as those of the first embodiment in terms of function and configuration are designated by the same reference numerals, and the description thereof is omitted.

The forceps plug device 50 includes an opening 51 fixed to the forceps port 17, and a forceps plug 52 detachably mounted on the opening 51. The opening 51 includes an opening body portion 51a fixed within the aperture 17a, and an opening tip portion 51b that protrudes toward the near side of the aperture 17a. The opening body portion 51a is fundamentally the same as the opening body portion 21a of the first embodiment. Additionally, the opening tip portion 51b is formed so as to have an external diameter that is somewhat smaller than the external diameter of the opening body portion 51a.

Figure 15:
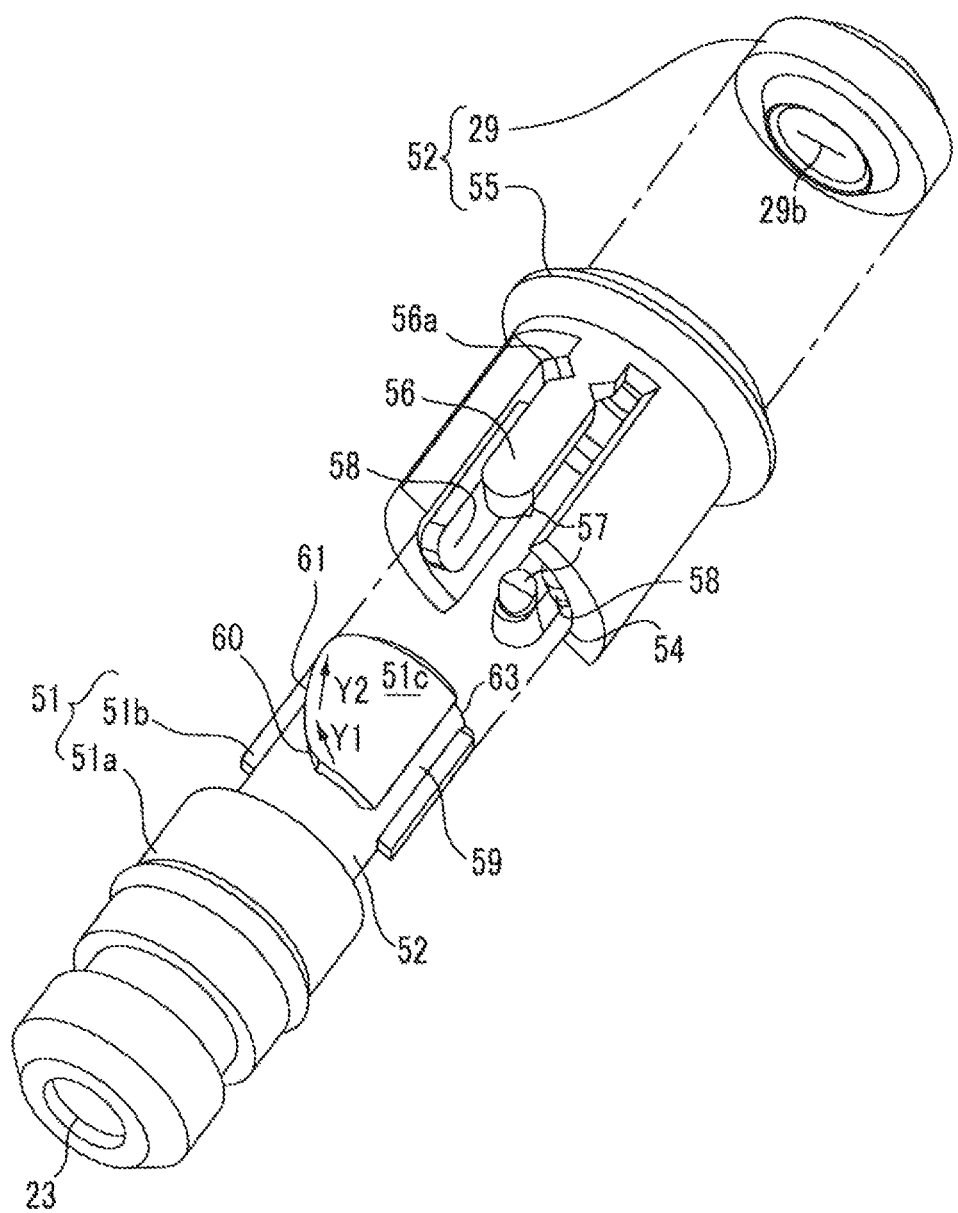
FIG. 15 is an exploded perspective view of the forceps plug device of the second embodiment seen from the opening side.
Figure 16:
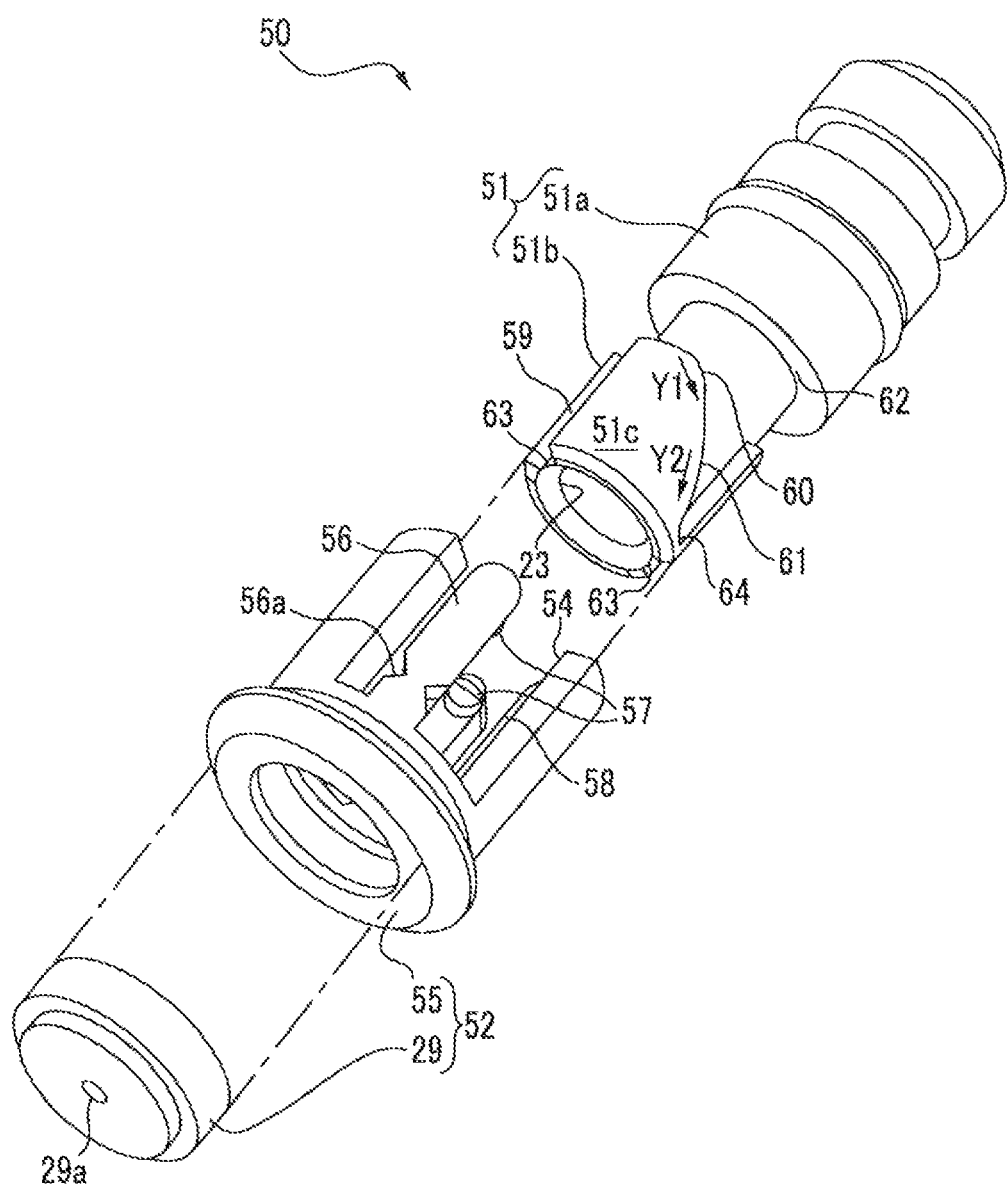
FIG. 16 is an exploded perspective view of the forceps plug device of the second embodiment seen from the forceps plug side.

As shown in FIGS. 15 and 16, the forceps plug 52 is formed from various elastic materials, and the opening tip portion 51b includes a tubular plug body 55 to which a fitting hole 54 fits, and the cap 29.

A pair of arms 56 that is different from the arm 31 of the first embodiment is formed at the plug body 55 by cutting out a portion of the outer periphery of the plug body. The arm 56 extends long in a direction parallel to the opening axial direction. A low-strength portion 56a is formed at a root portion of an arm 56 similarly to the low-strength portion 31a of the first embodiment. Thereby, the low-strength portion 56a breaks when the deflection of the arm 56 exceeds a certain size. Moreover, the tip portion of the arm 56 is formed with a boss 57 that protrudes along the outer peripheral surface of the opening tip portion 51b.

Additionally, the inner surface of the plug body 55 is formed with a pair of guide protrusions 58 that face each other with the central axis of the fitting hole 54 as a center.

The outer peripheral surface of the opening tip portion 51b is formed with a pair of guide grooves 59 that the guide protrusion 58 engages with the central axis of the inner conduit 23 as a center, a pair of cam grooves 60 for locking that locks the boss 57, and a pair of cam grooves 61 for removal that is connected to the cam groove 60 for locking and that the boss 57 engages when the forceps plug 52 is removed. Additionally, a rear end portion of the opening tip portion 51b is formed with an annular groove 62.

The guide groove 59 is formed at a position that is offset in the first circumferential direction with respect to the cam groove 60 for locking. The guide groove 59 extends to the annular groove 62 along the opening axial direction from the opening tip position 63 of the tip of the opening tip portion 51b, and the guide protrusion 58 is guided toward the tip direction or rear end direction. Thereby, the movement direction of the forceps plug 52 is limited to the direction parallel to the opening axial direction.

The cam groove 60 for locking has a shape that extends in an oblique direction Y1 that inclines with respect to the axial direction of the opening portion between the tip direction and the second circumferential direction from an inner wall face on the side of the tip direction in both the wall faces of the annular groove 62. The length of the cam groove 60 for locking is formed so as to be longer than the diameter of the boss 57. Additionally, the cam groove 60 for locking is positioned so as to be located on a straight line parallel to the opening axial direction passing through the boss 57 when the guide protrusion 58 engages the guide groove 59. Accordingly, while this engagement is maintained, the boss 57 and the cam groove 60 for locking are located on the same straight line parallel to the opening axial direction.

A opening outer peripheral surface 51c of the opening tip portion 51b between the cam groove 60 for locking and the tip of the opening tip portion 51b becomes a passage through which the boss 57 passes when the forceps plug 52 is attached. The opening outer peripheral surface 51c deflects the arm 56 in the shape of a circular arc via the boss 57 passing thereabove in a direction away from the opening outer peripheral surface 51c. The external diameter of the plug body 55 is adjusted so that the deflection of the low-strength portion 56a does not exceed an elastic limit.

Figure 17:
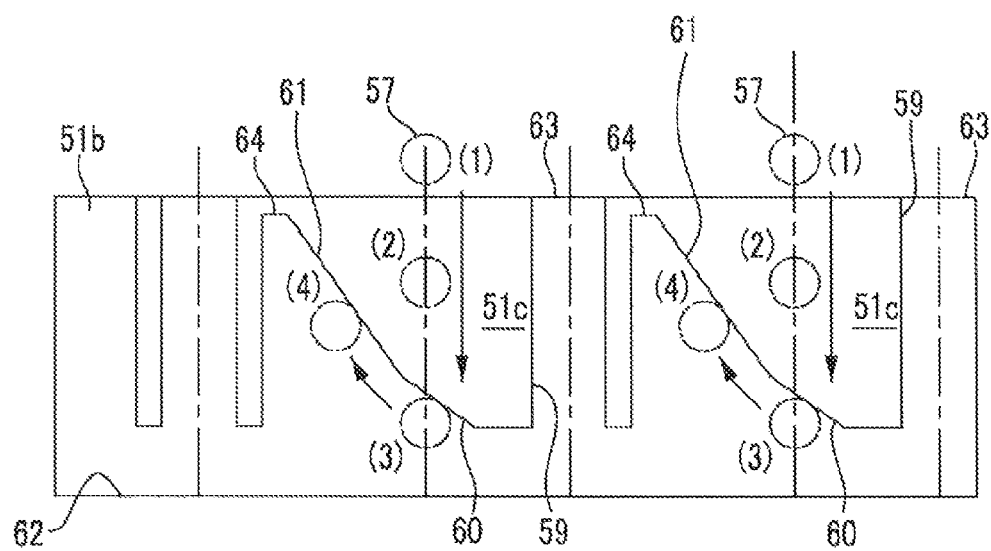
FIG. 17 is an explanatory view for explaining the movement path of a boss that moves along a groove formed in an outer peripheral surface of an opening.

The cam groove 61 for removal extends to a groove end point position 64 that is offset closer to the second circumferential direction than the cam groove 60 for locking at the tip of the opening tip portion 51b from the groove end point of the cam groove 60 for locking (refer to FIG. 17). The cam groove 61 for removal has a shape that extends in the oblique direction Y2 that inclines closer to the tip direction than the oblique direction Y1 that inclines with respect to the axial direction of the opening portion.

Such a cam groove 61 for removal guides the boss 57 toward the groove end point position 64 from the groove end point of the cam groove 60 for locking. Additionally, the cam groove 61 for removal deflects the arm 56 via the boss 57 when the boss 57 is guided. Moreover, the inclination angle or groove end point position 64 in the cam groove 61 for removal is adjusted so that the low-strength portion 56a breaks when the deflection thereof exceeds the elastic limit until the boss 57 reaches the groove end point position 64.

Next, the operation of the forceps plug 52 having the above configuration, particularly the attachment and removal processing of the forceps plug device 50 to/from the opening 51 will be described.

Figure 18:
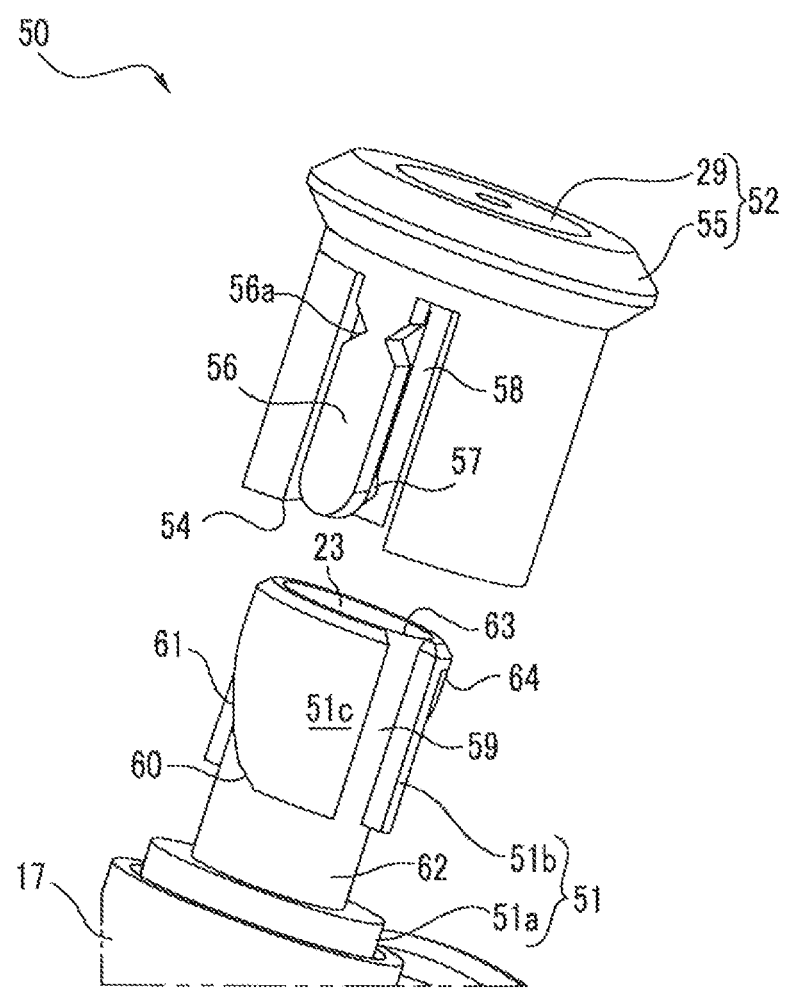
FIG. 18 is an explanatory view for explaining the positioning between a guide protrusion and a guide groove.

As shown by the number (1) in parentheses of FIG. 17 and as shown in FIG. 18, the positioning of the forceps plug 52 is first adjusted so that the center of the fitting hole 54 coincides with the center of the opening tip portion 51b, and then, the positioning of the forceps plug 22 is performed so that the guide protrusion 58 is located substantially above the opening tip position 63.

Figure 19:
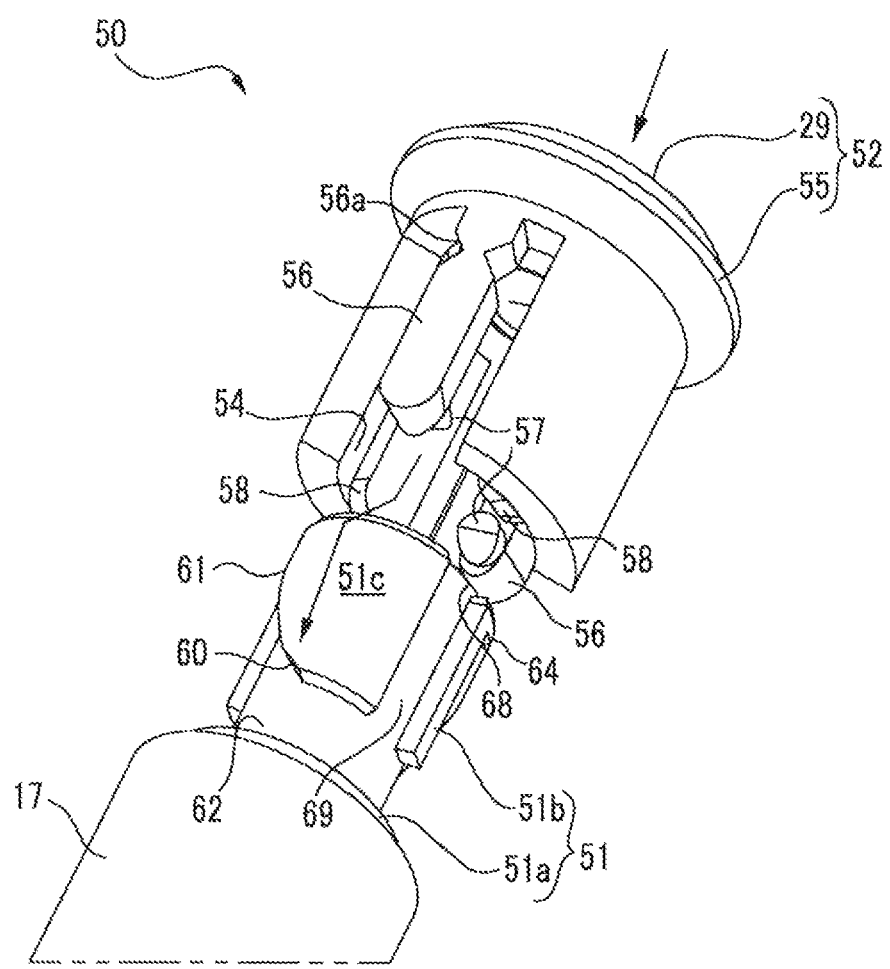
FIG. 19 is an explanatory view for explaining the manipulation of pushing the forceps plug.

As shown in FIG. 19, the forceps plug 52 is pressed against the opening tip portion 21b. Thereby, the tip of the opening tip portion 51b is inserted into the fitting hole 54, and the guide protrusion 58 is guided into the guide groove 59 from the opening tip position 63. As the guide protrusion 58 engages the guide groove 59, the alignment between the boss 57 and the cam groove 60 for locking is performed. Additionally, simultaneously when the guide protrusion 58 engages the guide groove 59, the boss 57 touches the tip of the opening tip portion 51b.

Figure 20:
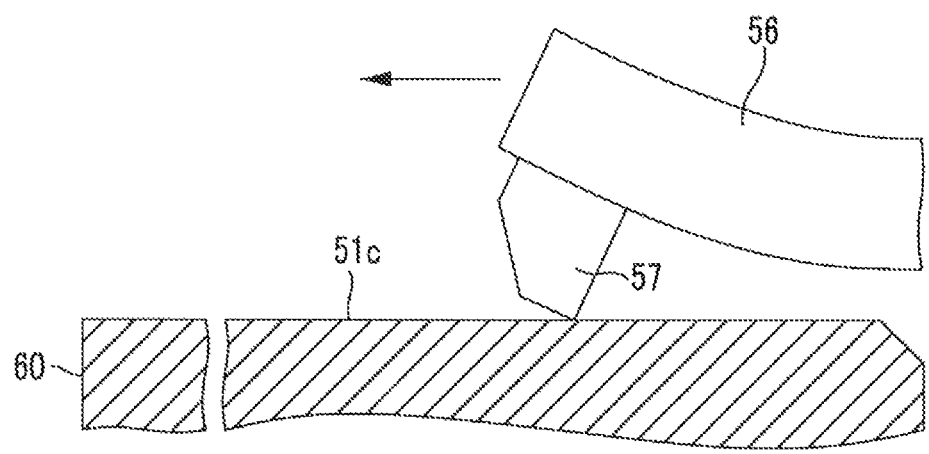
FIG. 20 is an explanatory view for explaining deflection of an arm when the forceps plug is attached.

Succeedingly, if the pressing manipulation is continued succeedingly, the forceps plug 52 is moved toward the rear end direction along the guide groove 59 by the guide protrusion 58, and the tip of the opening tip portion 51b is further inserted into the back of the fitting hole 54. Additionally, with this movement, as shown by the number (2) in parentheses of FIG. 17, and as shown in FIG. 20, the boss 57 rides on the opening outer peripheral surface 51c from the tip of the opening tip portion 51b, and the arm 56 deflects in the shape of a circular arc in a direction away from the opening outer peripheral surface 51c. Then, the arm 56 also moves toward the cam groove 60 for locking in a deflected state with the movement of the forceps plug 52 in the rear end direction. In this case, since the deflection of the low-strength portion 56a does not exceed an elastic limit, the low-strength portion 56a does not break.

Figure 21:
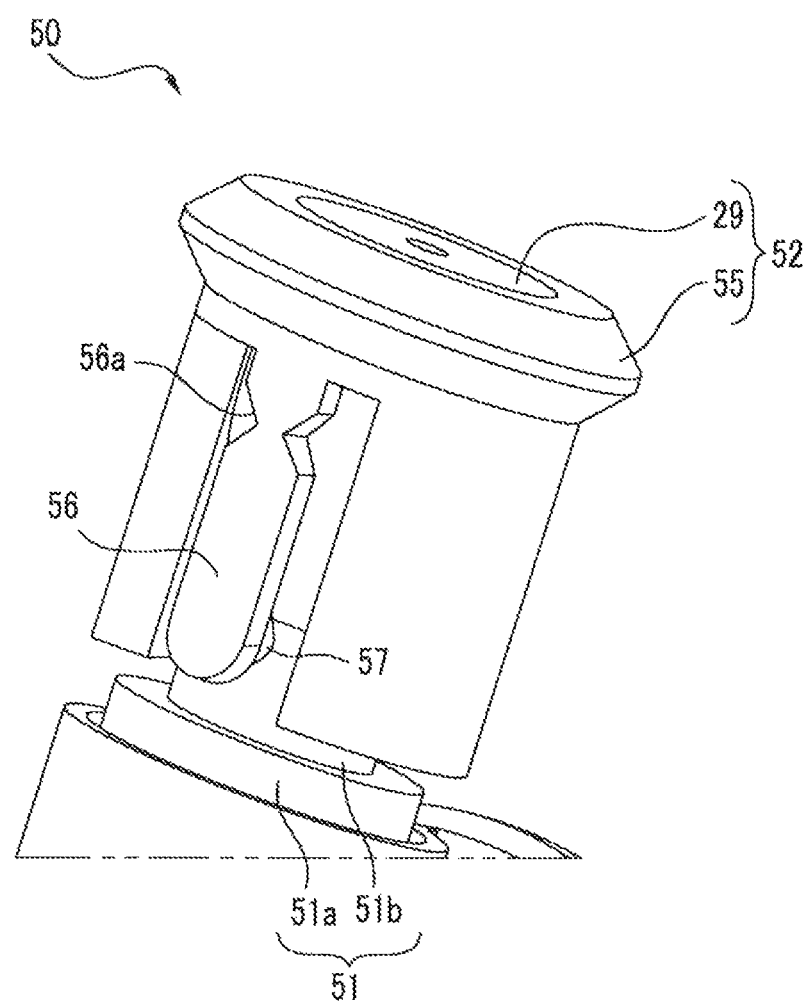
FIG. 21 is an explanatory view for explaining a state where the boss is locked to a cam groove for locking having a shape different from the first embodiment.

If the boss 57 rides over the opening outer peripheral surface 51c and reaches the cam groove 60 for locking as shown in the number (3) in parentheses of FIG. 17, and as shown in FIG. 21, the arm 56 is restored to its original shape. Thereby, the boss 57 is locked to the cam groove 60 for locking. Additionally, when the boss 57 reaches the cam groove 60 for locking, the fitting of the opening tip portion 51b to the fitting hole 54 is completed.

As the cam groove 60 for locking locks the boss 57, the forceps plug 52 is fixed to the opening 51. Additionally, since the guide protrusion 58 engages the guide groove 59 at this time, the rotation of the forceps plug 52 is regulated. Thereby, since the boss 57 is prevented from engaging the guide groove 59, the forceps plug 52 is prevented from separating from the opening 51 due to an erroneous operation.

The attachment processing of the forceps plug 52 is completed above. Then, after various kinds of treatment are performed by the treatment tool 14, removal processing of the forceps plug 52 is started. Specifically, the pulling manipulation of the forceps plug 52 in the tip direction is made.

The forceps plug 52 is moved toward the tip direction by the engagement between the guide protrusion 58 and the guide groove 59. Since the cam groove 60 for locking has a shape that inclines in the oblique direction Y1 shown in FIG. 15, the locking of the boss 57 caused by the cam groove 60 for locking is released, and the boss 57 is guided into the cam groove 61 for removal.

Figure 22:
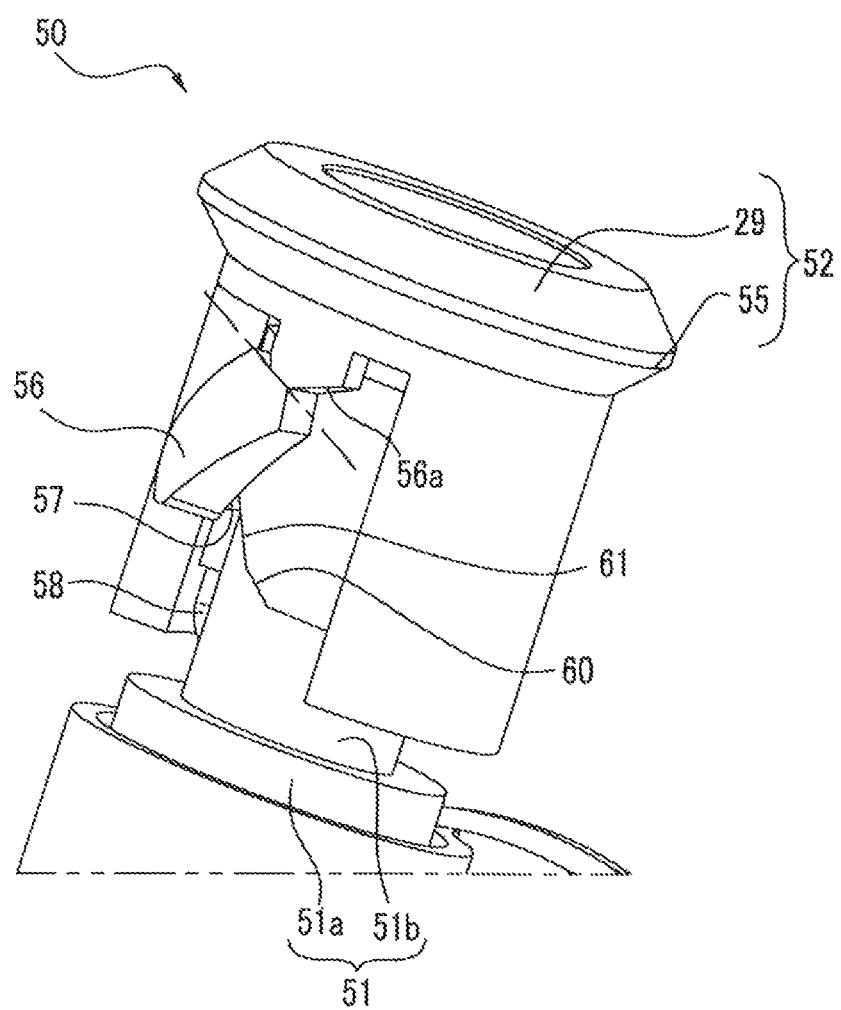
FIG. 22 is an explanatory view for explaining a state when the boss is guided along a cam groove for removal having a shape different from the first embodiment.

If the forceps plug 52 is succeedingly moved in the tip direction as shown in the number (4) in parentheses of FIG. 17, and as shown in FIG. 22, the boss 57 moves in a direction that turns to the groove end point position 64 along the cam groove 61 for removal. The arm 56 moves in the shape of a circular arc toward the second circumferential direction with the movement of the boss 57, and this amount of deflection increases gradually as the travel distance of the boss 57 increases. Then, the deflection of the low-strength portion 56a exceeds an elastic limit, and the low-strength portion 56a breaks until the boss 57 reaches the groove end point position 64. Thereby, the forceps plug 52 is brought into a free state with respect to the opening 51, and the forceps plug 52 is removed from the opening 51.

Since the arm 56 of the forceps plug 52 removed from the opening 51 is brought into a broken state, the forceps plug cannot be fixed to the opening 51 similarly to the first embodiment. As a result, the same effects as the first embodiment are obtained.

In the above respective embodiments, description has been made by exemplifying the cam groove 37 or 61 for removal as a cam groove that guides the boss 33 or 57 so that the arm 31 or 56 breaks at the time of the removal manipulation of the forceps plug 22 or 52. However, if the arm can be broken, the shape and length thereof is not particularly limited. Additionally, the shape of the arm provided at the forceps plug may be suitably changed according to changes in the shape or length of the cam groove. Moreover, the number of various grooves to be formed in the outer peripheral surface of the opening, and the number of arms to be provided at the forceps plug may be suitably increased or decreased.

In the above respective embodiments, description has been made by exemplifying the forceps plug 22 to be mounted on the opening 21 of the forceps port 17. However, the present invention can also be applied to a forceps plug to be directly mounted on the aperture 17a of the forceps port 17.

In the above respective embodiments, description has been made by exemplifying the forceps plug 22 to be mounted on the opening 21 that leads to the forceps channel 16. For example, however, the present invention can be applied to various kinds of channels disposed inside the endoscopes 10, such as a suction channel and a water supply and air supply channel, or a plug body unit mounted on the opening portion that leads to the inner conduit.

In the above respective embodiments, description has been made by exemplifying the endoscope 10 to be inserted into the tracheal. For example, however, the present invention can be applied to various endoscopes for medical purposes, such as a large-intestine endoscope to be inserted into the large intestine, an endoscope used for other applications, such as an industrial application, and the like.

What is claimed is:

1. A plug device provided at an outer surface of an endoscope and having a tubular opening portion that leads to a channel within the endoscope and a plug body unit detachably attached to the opening portion, the plug device comprising:
    a tubular plug body provided at the plug body unit and having a fitting hole to which the opening portion fits;
    an arm formed by cutting out a portion of the plug body and extending along an outer peripheral surface of the opening portion fitting into the fitting hole;
    a boss provided at a tip portion of the arm and protruding toward an outer peripheral surface of the opening portion;
    a locking groove formed at the outer peripheral surface of the opening portion and locking the boss when the opening portion fits to the fitting hole; and
    a cam groove formed at the outer peripheral surface of the opening portion continuously with the locking groove and guiding the boss in a direction in which the deflection of the arm increases from the locking groove with the displacement of the plug body unit by removal manipulation of the plug body unit,
    wherein an elastic limit of the arm is greater than a force which is applied by the deflection of the arm until the boss is locked by the locking groove and less than a force which is applied by the deflection of the arm until the boss reaches an end point of the cam groove
    wherein the boss is guided until the boss reaches an end point of the cam groove, and when the deflection of the arm exceeds an elastic limit, the arm breaks.

2. The plug device according to claim 1,
    wherein the outer peripheral surface of the opening portion is provided with a guide groove that extends to the locking groove in an oblique direction that inclines with respect to the axial direction of the opening portion from a opening portion tip position in the tip of the opening portion that is offset in the first circumferential direction with respect to the locking groove, and that guides the boss to the locking groove, and
    wherein the boss engages the guide groove from the opening portion tip position, and moves to the locking groove along the guide groove when the plug body unit is rotated after the engagement in a second circumferential direction opposite to the first circumferential direction.

3. The plug device according to claim 2,
    wherein the fitting is completed when the opening portion proceeds to the back of the fitting hole and the boss moves to the locking groove, with the movement of the boss along the guide groove.

4. The plug device according to claim 2,
    wherein the guide groove has a shape that maintains the deflection of the arm accompanying the movement of the boss within the elastic limit.

5. The plug device according to claim 3,
    wherein the guide groove has a shape that maintains the deflection of the arm accompanying the movement of the boss within the elastic limit.

6. The plug device according to claim 2,
    wherein the locking groove extends toward the tip of the opening portion from the end point of the guide groove.

7. The plug device according to claim 3,
    wherein the locking groove extends toward the tip of the opening portion from the end point of the guide groove.

8. The plug device according to claim 2,
    wherein the cam groove extends from the locking groove in the oblique direction that inclines with respect to the axial direction of the opening portion to a groove end point position that is offset closer to the second circumferential direction at the rear end side of the opening portion than the locking groove, and
    wherein as the plug body unit is rotated in the second circumferential direction after the locking of the boss by the locking groove, the boss is guided to the cam groove from the locking groove, and moves toward the groove end point position along the cam groove.

9. The plug device according to claim 3,
    wherein the cam groove extends from the locking groove in the oblique direction that inclines with respect to the axial direction of the opening portion to a groove end point position that is offset closer to the second circumferential direction at the rear end side of the opening portion than the locking groove, and
    wherein as the plug body unit is rotated in the second circumferential direction after the locking of the boss by the locking groove, the boss is guided to the cam groove from the locking groove, and moves toward the groove end point position along the cam groove.

10. The plug device according to claim 1,
    wherein the outer peripheral surface of the opening portion is provided with a guide groove that extends in the axial direction of the opening portion toward the rear end of the opening portion from a opening portion tip position in the tip of the opening portion that is offset closer to the first circumferential direction with respect to the locking groove,
    wherein the inner surface of the plug body is provided with a guide protrusion that engages the guide groove from the opening portion tip position,
    wherein the boss and the locking groove are located on the same straight line parallel to the axial direction of the opening portion when the guide protrusion engages the guide groove, and
    wherein the boss rises over the outer peripheral surface of the opening portion from the tip of the opening portion and moves to the locking groove as the plug body unit is moved in a first direction that faces the rear end side of the opening portion in a state where the guide protrusion engages the guide groove.

11. The plug device according to claim 10,
    wherein the cam groove extends from the locking groove in the oblique direction that inclines with respect to the axial direction of the opening portion to a groove end point position that is offset to the second circumferential direction opposite to the first circumferential direction and closer to the tip of the opening portion than the locking groove, and wherein as the plug body unit is moved in the second circumferential direction opposite to the first circumferential direction after the locking of the boss by the locking groove, the boss is guided to the cam groove from the locking groove, and moves toward the groove end point position along the cam groove.

12. The plug device according to claim 1,
wherein the channel is a treatment tool channel through which a treatment tool is inserted.

13. The plug device according to claim 2,
wherein the channel is a treatment tool channel through which a treatment tool is inserted.

14. The plug device according to claim 3,
wherein the channel is a treatment tool channel through which a treatment tool is inserted.

15. The plug device according to claim 10,
wherein the channel is a treatment tool channel through which a treatment tool is inserted.

16. The plug device according to claim 11,
wherein the channel is a treatment tool channel through which a treatment tool is inserted.

17. An endoscope comprising:
an insertion part to be inserted into a body to be examined;
a channel to be inserted through the inside of the insertion part, and
the plug device according to claim 1.

18. An endoscope comprising:
an insertion part to be inserted into a body to be examined;
a channel to be inserted through the inside of the insertion part; and
the plug device according to claim 2.

19. An endoscope comprising:
an insertion part to be inserted into a body to be examined;
a channel to be inserted through the inside of the insertion part; and
the plug device according to claim 3.

20. An endoscope comprising:
an insertion part to be inserted into a body to be examined;
a channel to be inserted through the inside of the insertion part; and
the plug device according to claim 10.

21. An endoscope comprising:
an insertion part to be inserted into a body to be examined;
a channel to be inserted through the inside of the insertion part; and
the plug device according to claim 11.

* * * * *